United States Patent [19]

Zimble

[11] Patent Number: 5,085,585
[45] Date of Patent: Feb. 4, 1992

[54] DENTAL MEDICAMENT APPLICATOR AND METHOD OF USE

[76] Inventor: Alan W. Zimble, 6 McDaniel Ave., Wilmington, Del. 19803

[21] Appl. No.: 650,627

[22] Filed: Feb. 5, 1991

[51] Int. Cl.⁵ .................. A61G 17/02; A61C 5/00
[52] U.S. Cl. .................................. 433/80; 433/215
[58] Field of Search ............... 433/80, 89, 136, 215

[56] References Cited

U.S. PATENT DOCUMENTS

| | | | |
|---|---|---|---|
| 2,257,709 | 10/1938 | Anderson | 128/861 |
| 2,707,951 | 5/1955 | Shackelford | 128/861 |
| 2,800,898 | 7/1957 | Greenblum | 128/861 |
| 3,107,668 | 10/1963 | Thompson | |
| 3,527,218 | 9/1970 | Westline | 433/80 |
| 3,527,219 | 9/1970 | Greenberg | 433/215 |
| 3,624,909 | 5/1970 | Reenberg | 433/80 |
| 3,955,281 | 5/1975 | Weitzman | 433/80 |
| 4,064,628 | 12/1977 | Weitzman | 433/80 |
| 4,106,501 | 8/1978 | Ozbey | 433/80 |
| 4,138,814 | 2/1979 | Weitzman | 433/215 |
| 4,531,914 | 7/1985 | Spinello | 433/136 |
| 4,544,354 | 10/1985 | Gores et al. | 433/42 |
| 4,560,351 | 12/1985 | Osborne | 433/80 |
| 4,856,991 | 8/1989 | Breads | 433/6 |

FOREIGN PATENT DOCUMENTS 93116 2/1922 Switzerland ................... 433/80

*Primary Examiner*—John A. Wilson
*Assistant Examiner*—Cindy A. Cherichetti
*Attorney, Agent, or Firm*—Connolly & Hutz

[57] ABSTRACT

A dental medicant applicator includes a U-shaped body member having a base portion with an upstanding peripheral wall. A shoulder is formed near the top edge of the wall. Medicament is placed in the base portion of the applicator. When the applicator is mounted in place the medicament spreads along the teeth. Continued mounting movement of the applicator results in the shoulder forcing the gums outwardly to expose the gum pocket so that the medicament is also deposited into the gum pocket.

3 Claims, 1 Drawing Sheet

DENTAL MEDICAMENT APPLICATOR AND METHOD OF USE

BACKGROUND OF THE INVENTION

The invention is directed to the application of a dental medicament subgingivally along the root of a gum pocket. Various devices and techniques exist which have as their aim the application of a medicament, such as a fluoride gel into a gum pocket. Generally, these devices and techniques are complicated with questionable effectiveness.

It would be desirable if a device could be provided which is simple in structure and which conveniently and reliably functions to apply such a medicament into the gum pocket.

SUMMARY OF THE INVENTION

An object of this invention is to fulfill the above needs.

In accordance with this invention, an applicator is provided in the form of a U-shaped member having an upstanding peripheral wall with a shoulder formed near the top edge of the peripheral wall. In use, a suitable medicament would be deposited in the base of the U-shaped member. As the member is mounted in place the medicament is forced to spread along the teeth. Continued mounting movement of the member results in the shoulder causing the gum to be forced outwardly so as to expose the gum pocket whereby the medicament would also be deposited into the gum pocket.

THE DRAWINGS

FIG. 1 is a top plan view of a dental medicament applicator in accordance with this invention;

FIGS. 2 and 3 are cross-sectional views taken through FIG. 1 along the lines 2—2 and 3—3; and FIGS. 4 and 5 are cross-sectional views similar to FIG. 3 in different phases of operation.

DETAILED DESCRIPTION

Figure 1:
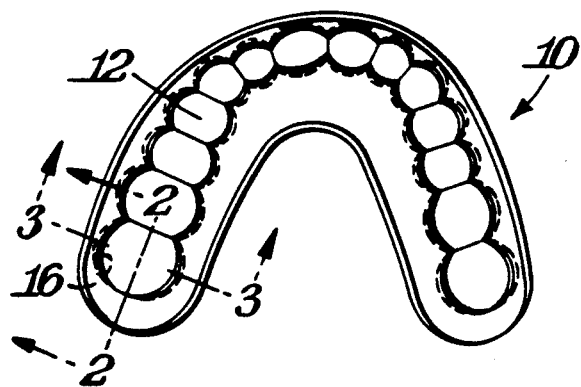

As illustrated a dental medicament applicator 10 is in the form of a body member having a U-shaped base portion 12 with an upstanding peripheral wall 14 extending labially and lingually. The peripheral wall 14 has an inner surface 16 and an outer surface 18 with a top surface 20. A shoulder 22 is peripherally formed near the upper or apical edge of the top surface 20. Shoulder 22 includes an upper corner 24.

Applicator 10 may be formed using conventional known techniques for forming dental applicators and orthodontic positioners. For example, by conventional, accurate impression techniques a plaster model would be created to reproduce the tooth and gum structure of the patient to create a mold of the mouth. The plaster model would then be prepared by scribing a groove of approximately 2 mm wide and 2 mm deep around the periphery of all existing teeth at the juncture where the teeth meet the gum. The groove could be scribed either manually with a hand instrument or mechanically with a rotating instrument. A collar would be formed by heat or vacuum forming which would slide over the tooth contour undercut. The collar would correspond to shoulder 22. The inner surface 16 of applicator 10 would thereby accurately conform to the tooth structure of the patient.

Figure 3:
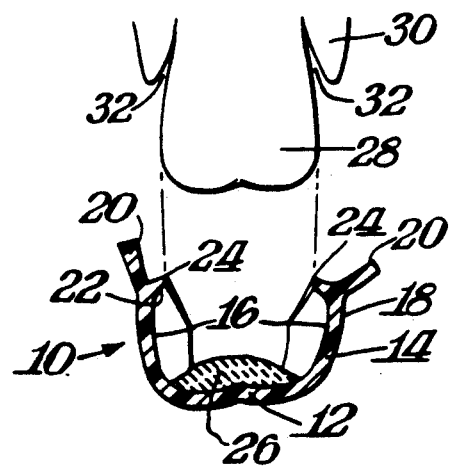
Figure 2:
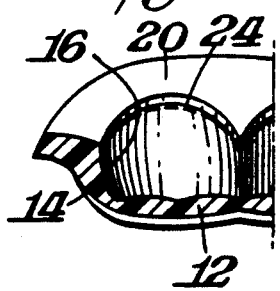

FIG. 3 shows the first stage in the use of applicator 10. As indicated therein, the trough or channel formed by U-shaped applicator 10 is filled about half way with a medicament 26 such as an anti-bacterial gel. A suitable gel would for example be a fluoride gel or any other therapeutic agents. Applicator 10 would be disposed in line with the tooth 28 of the patient and gums 30 with gum pocket 32 located between the tooth 28 and gum 30. Applicator 10 is mounted on the teeth by being snapped over the teeth. Because of the close fit of applicator 10 the medicament begins to spread along the inner surface 16 to coat the outer surface of the teeth as shown in its early stage of mounting in FIG. 4. Continued mounting movement of applicator 10 on tooth 28 results in the entire teeth surfaces being coated with the medicament. As shoulder or collar 22 reaches the gum pocket the corner 24 of shoulder or collar 22 causes the gum to be forced outwardly thereby sufficiently exposing the gum pocket 32 to result in medicament being forced into gum pocket 32. Accordingly, the medicament is forced subgingivally along the root of the gum into the gum pocket.

Applicator 10 may be made of any known materials conventionally used in the manufacture of dental positioners or mouth guards. A material is selected so that when applicator 10 snaps over the teeth, applicator 10 retains its shape and closely fits on the teeth with collar 22 fitting in the gum pocket to assure that the gel enters and remains in the gum pocket.

A key feature of this invention is the forming of applicator 10 to closely fit the anatomy of the teeth, gums and gum pockets. As previously indicated, conventional dental techniques could be used to assure the proper fit. For example, impression material could be used to obtain a mold. It is important that the mold is made to extend sufficiently so that the wash material goes under the gums. As a result, the mold includes not only the teeth anatomy but also includes the gum surface including the gum pocket. A thin line would result at the entrance of the gum pocket. The line would be mechanically widened to give sufficient thickness so that when the applicator 10 is formed from injection or vacuum molding the thickened line would correspond to collar 22.

Figure 4:
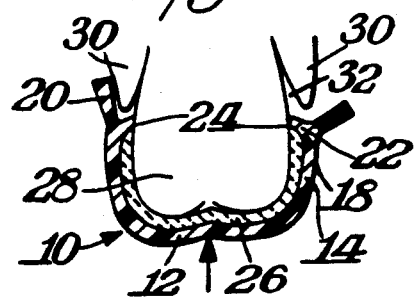
Figure 5:
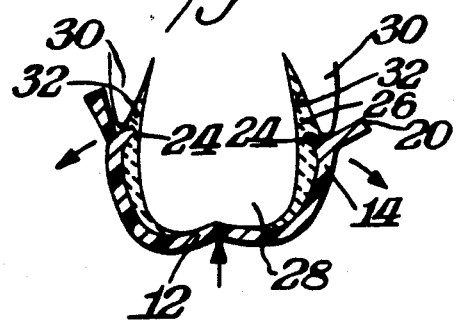

As is shown in FIGS. 4–5 collar 22 has a wedge shaped cross-section on each of the inner surfaces of the labial and lingual wall portions of peripheral wall 14. The wedge shaped collars on the lingual wall portion and on the labial wall portion are inclined toward each other. The distance between the lingual wall portion and the labial wall portion at the points of the collars which penetrate the gum pocket is closer than the distance between the wall portions immediately above and immediately below the collars at the anatomical areas of each tooth.

As can be appreciated, applicator 10 thus provides a convenient means for automatically applying a medicament such as a fluoride gel subgingivally along the root as well as along the teeth. This is accomplished by an applicator which is simple in construction and thus may be readily manufactured at low cost. During the mounting of applicator 10 the upper corner or edge 24 is disposed at the entrance to the gum pocket 32 at the inner surface of gum 30. While applicator 10 is being moved along the surface of the teeth, the medicament forces the resilient applicator to deflect outwardly. The deflection near the upper edge of applicator 10 causes the gum to deflect slightly outwardly by the fact that inner edge 24 is located on the inner surface of the gum and the inner edge is moved outwardly by the flowing medicament 26. As illustrated, collar 22 is formed to conform to the anatomy of gum 30 so that the outward deflection of collar 22 assures that gum pocket 32 will not be obstructed when the medicament 26 is to be applied into the gum pocket since deflection of collar 22 assures a movement of gum 30 in an outward direction.

What is claimed is:

1. A customized dental medicament applicator comprising a trough shaped body member made of a resilient material and having a U-shaped base portion, a peripheral wall extending outwardly along the complete periphery of said base portion, said peripheral wall including an apical edge and a labial wall portion and an oppositely disposed lingual wall portion said labial wall portion having an outer surface and an inner surface, said lingual wall portion having an outer surface and an inner surface, said inner surfaces being contoured to conform to the anatomy of the teeth of the individual user, the contour of each of said inner surfaces including means in the form of a peripheral collar located near said apical edge to be positioned at the gum pockets when said applicator is mounted to the teeth, said collar having a wedge shaped elevational cross section, said wedge shaped collars on said lingual wall portion and on said labial wall portion being inclined toward each, each of said wedge shaped cross sections having a point disposed for penetrating the gum pocket, the distance between said lingual wall portion and said labial wall portion at said points of said collars being closer than the distance between said wall portions immediately above and immediately below said collars at the anatomical area of each tooth whereby said points of said collars may be disposed in the gum pockets on each side of each tooth so that a medicament in said member may be forced along the teeth and into the gum pockets when said applicator is snapped on to the teeth.

2. The applicator of claim 1 in combination with a medicament in said body member.

3. A method of applying a medicament subgingivally along the root in a gum pocket comprising providing a U-shaped applicator having an outwardly extending peripheral collar near the upper surface of its upstanding peripheral wall on the outer surface of the peripheral wall, disposing a medicament into the applicator, mounting the applicator on the teeth of a patient with the inner surface of the peripheral wall being along the teeth to spread the medicament along the teeth as the applicator is being applied, and the collar forcing the gum outwardly to expose the gum pocket whereby medicament is forced into the gum pocket upon the completion of mounting the applicator.

* * * * *